United States Patent
Tomomatsu et al.

(10) Patent No.: US 6,775,899 B1
(45) Date of Patent: Aug. 17, 2004

(54) METHOD FOR INSPECTING PRINTING STATE AND SUBSTRATE

(75) Inventors: Michinori Tomomatsu, Fukuoka (JP); Masayuki Mantani, Fukuoka (JP); Takaaki Sakaue, Fukuoka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/576,716

(22) Filed: May 23, 2000

(30) Foreign Application Priority Data

May 24, 1999 (JP) .......................................... 11-142871

(51) Int. Cl.[7] ..................... G01N 21/596; G01R 31/304; G01R 31/309
(52) U.S. Cl. ..................... 29/593; 73/865.8; 356/237.5; 382/147
(58) Field of Search ................... 29/593; 73/865.8–866, 73/150 A–150 R; 428/8, 543; 250/559.44; 356/237.5; 382/147, 150; 324/501, 750–753, 763; 438/14, 16

(56) References Cited

U.S. PATENT DOCUMENTS

| | | | | |
|---|---|---|---|---|
| 1,825,796 A | * | 10/1931 | Himmel ........................ 428/201 |
| 2,521,954 A | * | 9/1950 | Tuttle et al. ............. 250/226 X |
| 4,165,465 A | * | 8/1979 | Kanatani et al. ........ 250/559.44 |
| 4,344,683 A | | 8/1982 | Stemme ........................ 354/106 |
| 4,472,738 A | * | 9/1984 | Hada et al. ........... 356/237.5 X |
| 4,488,808 A | * | 12/1984 | Kato ............................ 356/73 |
| 4,685,139 A | * | 8/1987 | Masuda et al. ..... 250/559.44 X |
| 4,719,494 A | * | 1/1988 | Shiota .......................... 355/77 |
| 4,878,753 A | | 11/1989 | Nestmeier .................... 356/237 |
| 5,027,295 A | * | 6/1991 | Yotsuya ....................... 382/147 |
| 5,428,459 A | * | 6/1995 | Asai ............................ 358/449 |
| 5,608,816 A | * | 3/1997 | Kawahara et al. ...... 382/147 X |
| 5,809,642 A | | 9/1998 | Ishihara et al. ............... 29/840 |
| 6,256,112 B1 | * | 7/2001 | Kawano ................. 382/162 X |
| 6,286,202 B1 | * | 9/2001 | Asai et al. ................ 29/593 X |

FOREIGN PATENT DOCUMENTS

| | | | |
|---|---|---|---|
| EP | 0 466 013 | 1/1992 | .......... G01N/21/88 |
| EP | 0 779 774 | 6/1997 | |
| JP | 61-225638 | * 10/1986 | ................. 250/566 |
| JP | 3-244188 | 10/1991 | |
| JP | 4-279808 | 10/1992 | |
| JP | 5-200991 | * 2/1993 | .......... G01N/21/88 |
| JP | 8-101130 | * 4/1996 | .......... G01N/21/88 |
| JP | 8-110938 | * 4/1996 | ............. G06T/7/00 |

\* cited by examiner

*Primary Examiner*—Thomas P. Noland
(74) *Attorney, Agent, or Firm*—Wenderoth, Lind & Ponack, L.L.P.

(57) ABSTRACT

A test printing portion with a pattern dimension smaller than a minimum printing pattern dimension is formed on a substrate, and a printing state of this test printing portion is inspected after printing. Based on inspection results of the test printing portion, acceptability of the printing state of the entire substrate is judged. The test printing portion is created on a periphery of the substrate outside the printing pattern area or an unprinted space inside the printing pattern area. A detection device detects the test printing portion, and inspects its printing state. Based on the inspection results, the acceptability of the printing state of the entire substrate is judged. This enables the printing state to be easily inspected at low cost while securing a necessary decree of accuracy.

16 Claims, 5 Drawing Sheets

METHOD FOR INSPECTING PRINTING STATE AND SUBSTRATE

BACKGROUND OF THE INVENTION

1. Field of the Invention

The present invention relates to the field of methods for inspecting the printing state of materials printed on substrates, and substrates to be printed

2. Description of the Prior Art

In the manufacturing process of circuit substrates (hereinafter referred to as "substrates") on which electronic components are mounted, the mounting state is inspected to secure the reliability of each product. Normally, an appearance inspection is implemented using a camera for examining the soldering state of electronic components mounted on a substrate. CSPs (chip size packages) and BGAs (ball grid arrays) are bonded onto the substrate using bumps provided on the bottom face of electronic components. The normal appearance inspection method involves observing the upper face of the substrate, and thus is not effective for inspecting the mounting state of these types of components because the soldered portion is concealed by the electronic component itself after being mounted. Accordingly, the printing state of solder paste (hereafter referred to as "solder") on the substrate is inspected, instead of the appearance inspection, to ensure reliability.

In order to improve the reliability of the inspection itself, all printed points on the substrate should ideally be inspected in the above inspection of the printing state. However, inspection of all printed points would require a long time because the camera would need to move to each target portion to check and evaluate the printing state by visual recognition. This reduces productivity, and increases equipment costs, since an exclusive inspection apparatus would be needed.

SUMMARY OF THE INVENTION

The present invention aims to provide a method for inspecting the solder printing state at low cost while securing the necessary degree of accuracy.

The inspection method of the present invention is to inspect materials printed in a predetermined pattern on a substrate by detecting the printed state with a detection means.

In the present invention, a test printing portion having a pattern dimension smaller than a minimum printing pattern dimension of an actual pattern to be printed is provided on the substrate. After printing, the test printing portion is detected by the detection means for examining the printing state. According to the inspection results of the test printing portion, the printing state of the entire substrate is judged. The test printing portion is provided on a periphery of the substrate outside of the effective printing region, or a space region inside the effective printing region. The detection means detects the printing state of the test printing portion, and the printing state of the entire substrate is judged based on the inspection results. Accordingly, the present invention enables the printing state to be inspected at low cost while securing the necessary degree of accuracy.

DESCRIPTION OF THE PREFERRED EMBODIMENT

A preferred embodiment of the present invention is described next with reference to drawings.

Figure 1:
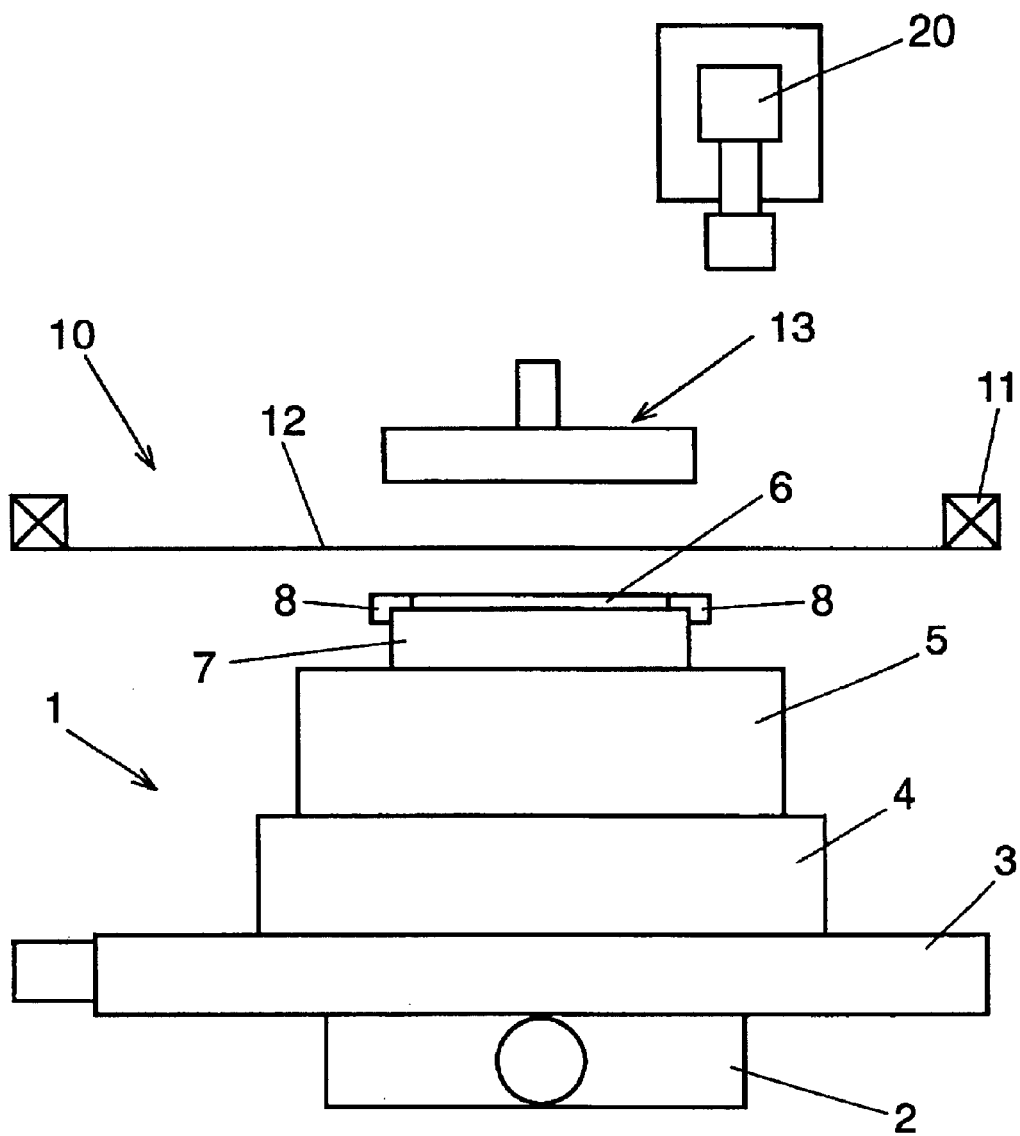
FIG. 1 is a schematic side view of a screen printing apparatus in accordance with a preferred embodiment of the present invention.

First, the configuration of a screen printing apparatus is described with reference to FIGS. 1 and 2. In FIG. 1, a substrate positioning unit 1 comprises a transfer table consisting of an X-axis table 2 and Y-axis table 3, a theta-axis table 4 provided on the transfer table, and a Z-axis table 5 disposed on a theta-axis table 4. A substrate support 7 is disposed on the Z-axis table 5 for holding a substrate 6 with a damper 8. The substrate 6 is for printing and is loaded onto the substrate positioning unit 1 by a loading conveyor 14 shown in FIG. 2. The position of the substrate 6 is adjustable by driving the substrate positioning unit 1. After printing, the substrate 6 is unloaded by an unloading conveyor 15.

A screen mask 10 is disposed over the positioning unit 1. The screen mask 10 comprises a frame 11 and screen 12. The substrate positioning unit 1 positions the substrate 6 against the screen 12 in such a way that the substrate 6 contacts the screen 12 from the bottom. A squeegee unit 13 is disposed over the screen mask 10 in a horizontally reciprocable fashion. Solder paste is supplied on the screen 12 when the bottom face of the screen 12 contacts the substrate 6. The squeegee unit 13 slides a squeegee on the surface of the screen 12 for printing solder onto the surface of the substrate 6 through an opening 12A (FIG. 2) in the screen 12.

A camera 20 is disposed over the screen mask 10. As shown in FIG. 2, the camera 20 moves horizontally in the XY direction according to an X-axis table 21 and Y-axis table 22. The camera 20 takes images of a recognition mark provided on the substrate as identification marks and a test printing portion set on the substrate 6. Details of the test printing portion are described later.

Figure 2:
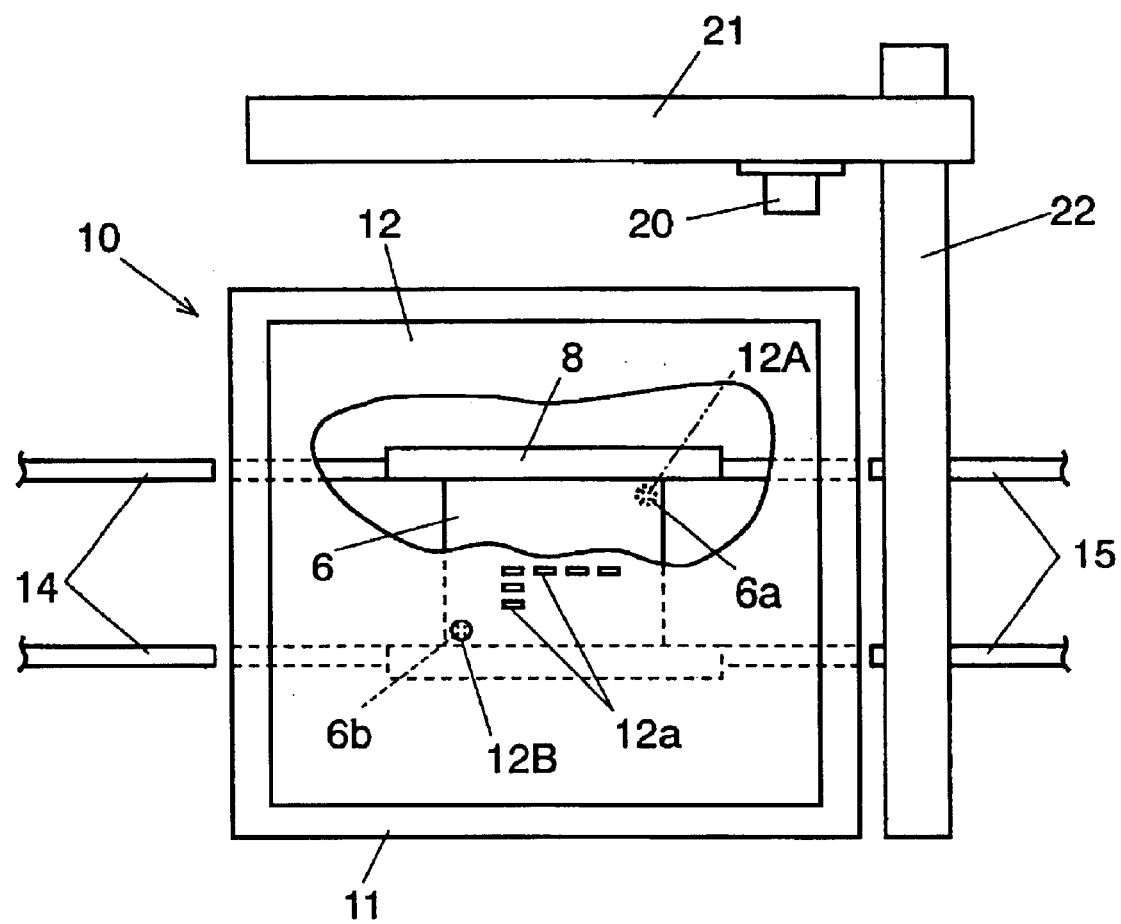
FIG. 2 is a plan view of the screen printing apparatus in accordance with the preferred embodiment of the present invention.

As shown in FIG. 2, recognition marks 6a and 6b, which are identification points on the substrate 6, are disposed at diagonal positions. Openings 12A and 12B corresponding to positions of the recognition marks 6a and 6b are created in the screen 12. In FIG. 2, the recognition mark 6b is located under the screen 12, and thus it is indicated with a broken line. If the substrate 6 is positioned correctly against the screen 12, the recognition marks 6a and 6b are visually recognizable through the openings 12A and 12B, and accordingly, their images can be recorded by the camera 20. The position of the substrate 6 is thus detected by checking the recognition marks 6a and 6b. The correction amount of the position of the substrate needed to mount electronic components is then calculated based on the results of detecting the positions of the recognition marks 6a and 6b.

Next, a screen mask for printing the test printing portion and patterns on the substrate 6 is described with reference to FIGS. 3A and 3B.

Figure 3A:
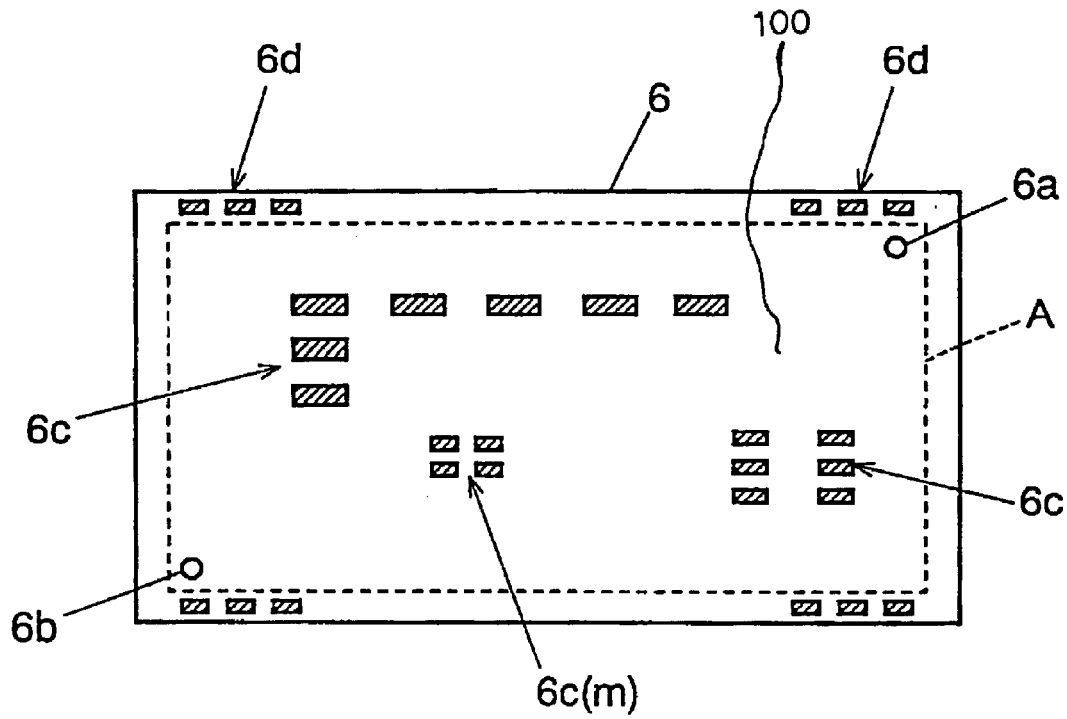
FIG. 3A is a plan view of a substrate in accordance with the preferred embodiment of the present invention.

As shown in FIG. 3A, the area inside the edge, from a predetermined width, of the substrate 6 is a printing pattern area 100 in which solder paste for mounting electronic components is printed. Lands 6c with a range of sizes are formed inside the printing pattern area 100. Solder paste is printed on these lands 6c by screen printing. A test printing pattern 6d for inspecting the printing state is provided on a periphery outside the printing pattern area 100 of the substrate 6.

Figure 3B:
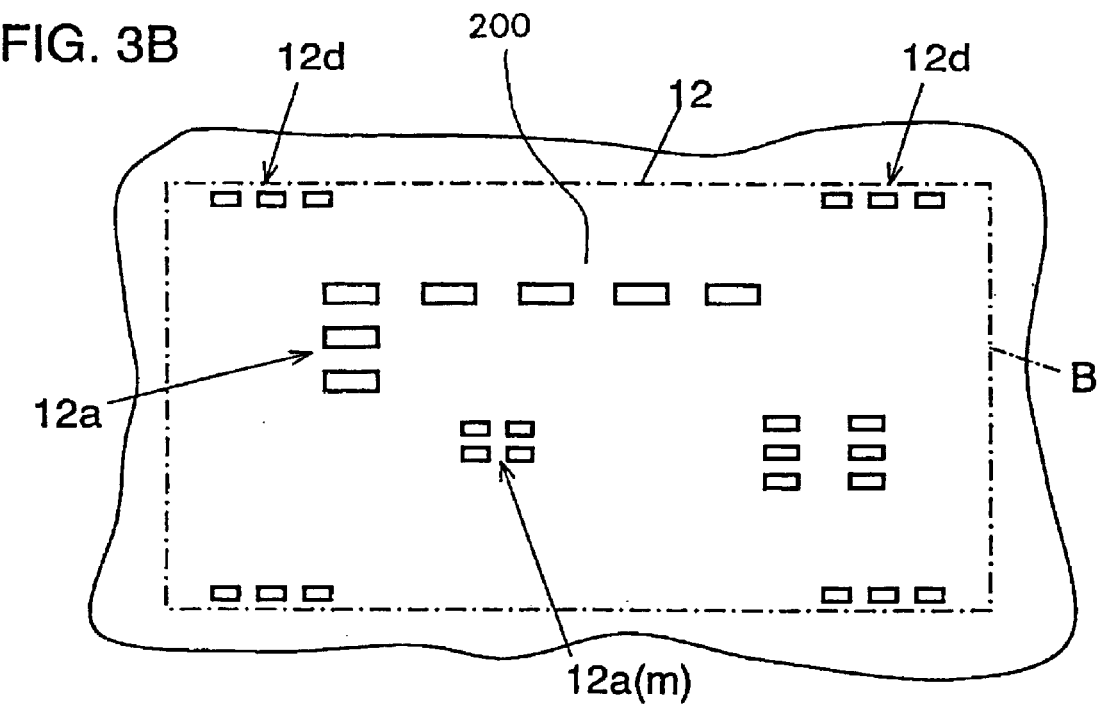
FIG. 3B is a plan view of a screen mask of the substrate in accordance with the preferred embodiment of the present invention.

FIG. 3B shows the screen 12 used for printing the substrate 6. An area 200, indicated with a one-dot chain line, corresponds to the substrate 6. Openings 12a corresponding to the screen pattern of lands 6c on the substrate 6 are created in the screen 12. The test printing pattern opening 12d corresponding to the test printing point 6d is provided at an area corresponding to the periphery of the substrate 6 outside the printing pattern area. The shape of the test printing pattern opening 12d is typically round or rectangular, depending on the land shape in the printing pattern of the target substrate.

The size of the test printing pattern opening 12d is smaller than the size of the solder printing pattern to be printed on the smallest land 6c (m) inside the printing pattern area 100. At present, the minimum size of the solder printing pattern practically used is approximately 0.4 mm. In this case, the size of the test printing pattern 12d is, for example, set to about 0.38 mm. The size of the test printing pattern 12d may be reduced as the size of the printing pattern shrinks further.

Figure 4:
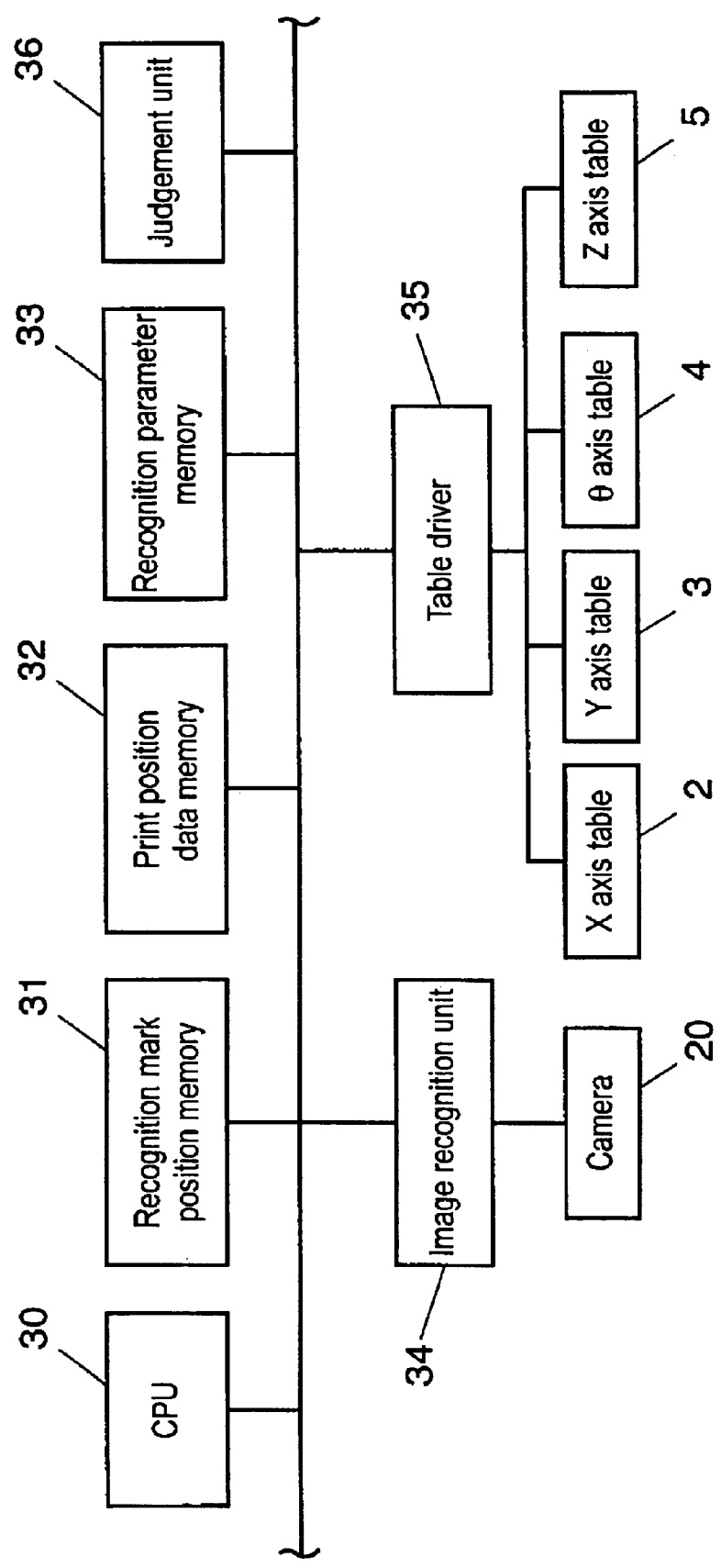
FIG. 4 is a block diagram illustrating the configuration of a control system of the screen printing apparatus in accordance with the preferred embodiment of the present invention.

Next, the configuration of the control system for the screen printing apparatus is described with reference to FIG. 4. In FIG. 4, a CPU 30 is a control unit which controls all other units described below. A recognition mark position memory 31 stores the positions of the recognition marks 6a and 6b on the substrate 6, openings 12A and 12B created in the screen 12, and the test printing portion. A recognition parameter memory 33 stores data such as the size of the recognition marks and test printing portion. A print position data memory 32 stores the required position correction amount for correcting the position of the substrate 6 with respect to the screen 12 during printing, and the position deviation of the test printing portion after printing. The required position correction amount and position deviation are obtained by identifying the recognition marks 6a and 6b, openings 12A and 12B, and test printing portion; and calculating the deviation in the position between the substrate 6 and screen 12.

The camera 20 captures images of the substrate 6 and screen 12, and the image recognizing unit 34 processes the image data obtained by the camera 20 regarding the positions of the recognition marks 6a and 6b and openings 12A and 12B. At the same time, the shape of the solder paste printed on the test printing portion is detected. A judgement unit 36 judges the printing state of the entire substrate based on the printing state of the test printing portion.

The judgement unit 36 first reads out the position data on the test printing portion stored in the recognition mark position memory 31, and recognition parameters for the shape and size of the test printing portion stored in the recognition parameter memory 33. Next, the judgement unit 36 compares the recognition result of a captured image of the test printing portion with the stored data for determining the acceptability of the printed state. The judgement is made by the position deviation of the test printing portion or printing state (the distribution of the printing area detected by optical recognition).

Figure 5A:
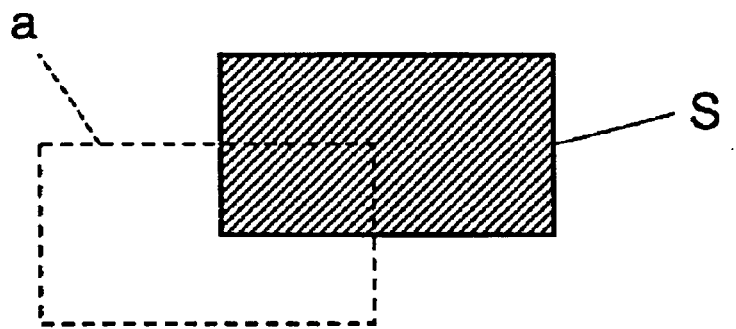
FIG. 5A illustrates a test printing portion during screen printing in accordance with the preferred embodiment of the present invention.
Figure 5B:
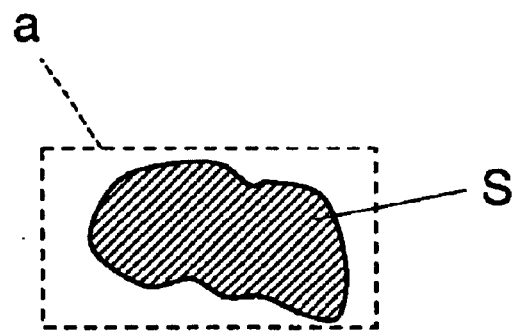
FIG. 5B illustrates the test printing portion during screen printing in accordance with the preferred embodiment of the present invention.
Figure 5C:
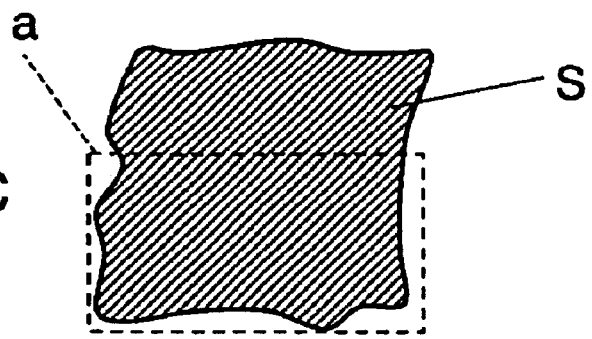
FIG. 5C illustrates the test printing portion during screen printing in accordance with the preferred embodiment of the present invention.

Judgment is made in accordance with the evaluation criteria given in FIGS. 5A–5C. More specifically, the items to be inspected are "positional deviations" as shown in FIG. 5A, which are deviations in the position of the printed solder from the predetermined printing area "a"; "unclear" shown in FIG. 5B, which shows insufficient amount of printed solder paste "s" compared to the predetermined amount (which is substituted by the printing area) in the predetermined printing area "a"; and "blur" shown in FIG. 5C which shows excess amount of solder "s" bulging out of the predetermined printing area "a", as distinct from "unclear". If one of the above items is out of the acceptable criteria, the judgement unit 36 determines that there is some kind of abnormality in the printing state.

A screen printing apparatus in the preferred embodiment of the present invention is configured as described above, and operation of the screen printing apparatus is described below.

After positioning the loaded substrate 6, solder is screen printed onto the substrate 6. The camera 20 is then moved over the substrate 6, and an image of the test printing pattern 6d is captured. The image data are recognized by the image recognition unit 34. Based on the recognition result, the image recognition unit 34 detects the printing state of the solder paste printed on the test printing portion. This detection result is judged by the judgement unit 36. If the judgement unit 36 judges that any one of the aforementioned items is not acceptable, an abnormality in the printing state is announced outside. Based on this notice, printing conditions are changed automatically or manually by the operator as required. If all items are acceptable, the judgement unit 36 judges that screen printing has been properly operated for the entire area on the inspected substrate.

The appropriateness of judging the printing state of the entire substrate based on inspection results of the test printing portion provided on just a portion of the substrate is based on the empirical knowledge of the inventors concerning solder printing quality. In general, the printing of highly viscous paste such as solder paste tends to cause a greater number of defects, such as "unclear" and "blur" as the size of the printing pattern reduces. Accordingly, if correct printing of the minimum printing pattern is confirmed, other printing patterns can be estimated to be satisfactorily printed. In addition, the central part of the screen mask is more likely to achieve a satisfactory printing state during screen printing, and the printing pattern close to the edge of the screen mask tends to cause defective printing.

Accordingly, the test printing portion which is smaller than the smallest printing pattern in the printing pattern area of the substrate is provided at a portion which is equivalent to the periphery of the screen mask, such as the outer peripheral area of the substrate outside the printed pattern area. If this test printing portion is correctly printed, it can be assumed that other printing portions on lands in the printing pattern area are satisfactorily printed.

The preferred embodiment is based on the above empirical knowledge. In other words, a simple inspection by means of a camera for detecting the substrate position and image processing function in the screen printing apparatus is performed for inspecting solder printing on the test printing portion on the periphery of the screen mask. This makes it possible to inspect solder printing with appropriate inspection accuracy without requiring an expensive and specially designed high-performance inspection apparatus, which would otherwise be required for inspecting the printing state of the entire substrate.

The above embodiment describes an example of providing the test printing pattern on the outer periphery of the substrate outside the printing pattern area 100. However, the test printing pattern of the present invention is not limited to these positions. For example, the test printing portion may be provided at an area where no land onto which solder paste is printed is present inside the printing pattern area 100, or at the unprinted area near the edge but inside the printing pattern area. The preferred embodiment also employs a camera for detecting the printing state. It is apparent that other instruments, such as a 3-D profilometer, may be used for inspection. Some other detection means include well known detection means using transmitted light or X-rays. These disclosed detection means may also be used.

As described above, the present invention provides a test printing portion smaller than the smallest printing pattern, and inspects the printing state by capturing an image of the test printing portion with the detection means. The printing state of the entire substrate is judged in accordance with the inspection results of the test printing portion. The test printing portion is provided in an area at high risk of showing defects, and printed under conditions creating a high risk of causing defects (e.g. reduced printing size).

Inspection of only the test printing portion on behalf of the printing state of the entire substrate to be inspected, without inspecting all printed points, enables one to secure necessary accuracy, and allows for solder printing inspection using a simple and inexpensive method.

The above embodiment describes the case of screen printing. However, the basic concept of the present invention, which is to provide a test point in an area most likely to show a defect under conditions most likely to cause a defect, and to inspect the test point instead of inspecting all points, is applicable to printing methods other than screen printing. Other printing methods include intaglio printing, relief printing, offset printing, and transcription printing.

The present invention is also applicable to the application of adhesives or solder to many points for fixing components to a substrate, typically using a dispenser. One example is to apply test adhesive using a nozzle with a smaller diameter than that of the dispenser nozzle. Ordinary skilled persons in the industry may apply the basic concept of the present invention in a wide range of other ways.

The inspection method of the present invention is not limited to the inspection of circuit substrates, but is also applicable to the manufacturing process of other products which involve a printing process.

What is claimed is:

1. A method for determining a printing state of material on a substrate, comprising:
   printing material onto a required portion of a substrate and a test portion of said substrate, wherein said test portion corresponds to an area of said substrate that is at a higher risk of resulting in a defect of said material when printed thereon than is said required portion when said material is printed thereon, and wherein said material is printed onto said test portion under a condition that has a high risk of resulting in a defect of said material when printed on said test portion; and
   judging a printing state of said material printed onto said required portion by inspecting a printing state of said material printed onto said test portion.

2. The method according to claim 1, wherein printing material onto a required portion of a substrate and a test portion of said substrate comprises using a mask such that said material is printed onto a specific location of said required portion of said substrate and a specific location of said test portion of said substrate.

3. The method according to claim 2, wherein said test portion corresponds to an area of said substrate that is at a higher risk of resulting in a defect of said material when printed thereon than is said required portion when said material is printed thereon by corresponding to an area of said substrate that is located outside of said required portion and along a peripheral edge of said substrate.

4. The method according to claim 3, wherein said material is printed onto said test portion under a condition that has a high risk of resulting in a defect of said material when printed on said test portion by printing said material under a condition that is at a higher risk of resulting in a defect of said material when printed on said test portion than is a condition under which said material is printed on said required portion.

5. The method according to claim 4, wherein said material is printed under a condition that is at a higher risk of resulting in a defect of said material when printed on said test portion than is a condition under which said material is printed on said required portion by printing said material through an opening in said mask onto said specific location of said test portion that is smaller in size than any opening in said mask through which said material is printed onto said specific location of said required portion.

6. The method according to claim 2, wherein said material is printed onto said test portion under a condition that has a high risk of resulting in a defect of said material when printed on said test portion by printing said material under a condition that is at a higher risk of resulting in a defect of said material when printed on said test portion than is a condition under which said material is printed on said required portion.

7. The method according to claim 1, wherein said test portion corresponds to an area of said substrate that is at a higher risk of resulting in a defect of said material when printed thereon than is said required portion when said material is printed thereon by corresponding to an area of said substrate that is located outside of said required portion and along a peripheral edge of said substrate.

8. The method according to claim 7, wherein said material is printed onto said test portion under a condition that has a high risk of resulting in a defect of said material when printed on said test portion by printing said material under a condition that is at a higher risk of resulting in a defect of said material when printed on said test portion than is a condition under which said material is printed on said required portion.

9. The method according to claim 8, wherein said material is printed under a condition that is at a higher risk of resulting in a defect of said material when printed on said test portion than is a condition under which said material is printed on said required portion by printing said material onto a location of said test portion that is smaller in size than any location of said required portion onto which said material is printed.

10. The method according to claim 1, wherein said material is printed onto said test portion under a condition that has a high risk of resulting in a defect of said material when printed on said test portion by printing said material under a condition that is at a higher risk of resulting in a defect of said material when printed on said test portion than is a condition under which said material is printed on said required portion.

11. A method for determining a printing state of material on a substrate, comprising:
 printing material onto a required portion of a substrate and a test portion of said substrate, wherein said test portion corresponds to an area of said substrate that is at high risk of resulting in a defect of said material when printed thereon, and wherein said material is printed onto said test portion under a condition that is at a higher risk of resulting in a defect of said material when printed on said test portion than is a condition under which said material is printed on said required portion.

12. The method according to claim 11, wherein said material is printed under a condition that is at a higher risk of resulting in a defect of said material when printed on said test portion than is a condition under which said material is printed on said required portion by printing said material onto a location of said test portion that is smaller in size than any location of said required portion onto which said material is printed.

13. The method according to claim 12, wherein said test portion corresponds to an area of high risk by corresponding to an area of said circuit board that is at a higher risk of resulting in a defect of said material when printed thereon than is said required portion when said material is printed thereon.

14. The method according to claim 11, wherein printing material onto a required portion of a substrate and a test portion of said substrate comprises using a mask such that said material is printed onto a specific location of said required portion of said substrate and a specific location of said test portion of said substrate.

15. The method according to claim 14, wherein said material is printed under a condition that is at a higher risk of resulting in a defect of said material when printed on said test portion than is a condition under which said material is printed on said required portion by printing said material through an opening in said mask onto said specific location of said test portion that is smaller in size than any opening in said mask through which said material is printed onto said specific location of said required portion.

16. The method according to claim 15, wherein said test portion corresponds to an area of high risk by corresponding to an area of said substrate that is at a higher risk of resulting in a defect of said material when printed thereon than is said required portion when said material is printed thereon.

* * * * *

UNITED STATES PATENT AND TRADEMARK OFFICE
CERTIFICATE OF CORRECTION

| | | |
|---|---|---|
| PATENT NO. | : 6,775,899 B1 | Page 1 of 1 |
| APPLICATION NO. | : 09/576716 | |
| DATED | : August 21, 2006 | |
| INVENTOR(S) | : Michinori Tomomatsu et al. | |

It is certified that error appears in the above-identified patent and that said Letters Patent is hereby corrected as shown below:

ON THE FRONT PAGE

In Item (56) References Cited "Foreign Patent Documents"

Change "JP 5-200991 2/1993 ....G01N/21/88" to --JP 5-200991 8/1993 ....G01N/21/88--.

Signed and Sealed this

Nineteenth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 6,775,899 B1
APPLICATION NO. : 09/576716
DATED : August 17, 2004
INVENTOR(S) : Michinori Tomomatsu et al.

It is certified that error appears in the above-identified patent and that said Letters Patent is hereby corrected as shown below:

ON THE FRONT PAGE

In Item (56) References Cited "Foreign Patent Documents"

Change "JP 5-200991  2/1993 ....G01N/21/88" to --JP 5-200991 8/1993 ....G01N/21/88--.

This certificate supersedes Certificate of Correction issued December 19, 2006.

Signed and Sealed this

Thirtieth Day of January, 2007

JON W. DUDAS
*Director of the United States Patent and Trademark Office*